US010454229B2

(12) United States Patent
Wolff

(10) Patent No.: US 10,454,229 B2
(45) Date of Patent: Oct. 22, 2019

(54) RACK MODULE AND RACK

(71) Applicant: Fresenius Vial SAS, Brézins (FR)

(72) Inventor: Rémy Wolff, Morette (FR)

(73) Assignee: Fresenius Vial SAS, Brézins (FR)

( * ) Notice: Subject to any disclaimer, the term of this patent is extended or adjusted under 35 U.S.C. 154(b) by 0 days.

(21) Appl. No.: 15/757,131

(22) PCT Filed: Oct. 5, 2016

(86) PCT No.: PCT/EP2016/073708
§ 371 (c)(1),
(2) Date: Mar. 2, 2018

(87) PCT Pub. No.: WO2017/060260
PCT Pub. Date: Apr. 13, 2017

(65) Prior Publication Data
US 2018/0287320 A1 Oct. 4, 2018

(30) Foreign Application Priority Data
Oct. 9, 2015 (EP) .................................... 15306596

(51) Int. Cl.
*A61M 5/172* (2006.01)
*H01R 31/00* (2006.01)
(Continued)

(52) U.S. Cl.
CPC ........... *H01R 31/005* (2013.01); *A61M 5/008* (2013.01); *A61M 5/1413* (2013.01);
(Continued)

(58) Field of Classification Search
USPC .......................................................... 604/65
See application file for complete search history.

(56) References Cited

U.S. PATENT DOCUMENTS 4,738,632 A * 4/1988 Schmidt ............... H05K 7/1441
361/729
5,885,109 A * 3/1999 Lee ...................... H01R 13/514
439/131
(Continued)

FOREIGN PATENT DOCUMENTS

DE 40 30 368 11/1991
DE 199 40 526 C1 7/2001
(Continued)

OTHER PUBLICATIONS

International Search Report and Written Opinion, counterpart International Appl. No. PCT/EP2016/073708 dated Dec. 16, 2016 (13 pages).

*Primary Examiner* — Hien D Vu
(74) *Attorney, Agent, or Firm* — Cook Alex Ltd.

(57) ABSTRACT

The invention concerns a rack module for forming a support column, such as a rack, by stacking at least two rack modules, the rack module having at least one site for receiving a device for administering a medical product, this site comprising at least one plug for electric current supply to the administering device and for data transfer. It is also provided with an inlet connector and an outlet connector for connecting two successive modules to each other, power lines and data transfer lines connecting the inlet connector with the plug of the sites on the one hand side and with the outlet connector on the other hand side. In order to improve the connection between the rack modules in order to make its use easier, it is suggested according to the invention that the inlet connector or the outlet connector is movable between a stocking position and a connected position, the movable connector being called mobile connector and the other connector being called second connector, wherein, when a second module is placed over or under the module, the mobile connector in the connected position is in con- (Continued)

Figure 1:
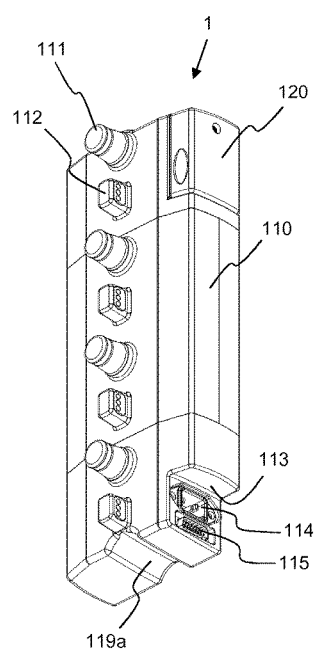

nection with the second connector of a second module placed over or under the module. This allows to stock in a safe position one of the connectors so that during the stocking and the handling of the module there is no risk for it to be damaged.

9 Claims, 4 Drawing Sheets

(51) Int. Cl.
    *A61M 5/14*     (2006.01)
    *H01R 9/24*     (2006.01)
    *A61M 5/00*     (2006.01)
    *H01R 13/60*     (2006.01)
    *H01R 35/00*     (2006.01)
    *A61B 50/22*     (2016.01)

(52) U.S. Cl.
    CPC ......... *A61M 5/1415* (2013.01); *H01R 9/2458* (2013.01); *H01R 13/60* (2013.01); *H01R 35/00* (2013.01); *A61B 50/22* (2016.02); *A61M 2205/82* (2013.01); *A61M 2205/8262* (2013.01); *H01R 2201/12* (2013.01)

(56) References Cited

U.S. PATENT DOCUMENTS

| | | | | |
|---|---|---|---|---|
| 5,941,846 | A * | 8/1999 | Duffy | A61M 5/1413 604/65 |
| 6,172,875 | B1 * | 1/2001 | Suzuki | G06F 1/183 361/679.4 |
| 6,193,655 | B1 * | 2/2001 | McGrath | H01R 13/005 128/897 |
| 7,399,205 | B2 * | 7/2008 | McNeely | A61B 5/0006 439/577 |
| 2007/0088249 | A1 | 4/2007 | Duffy et al. | |
| 2012/0185267 | A1 | 7/2012 | Kamen et al. | |

FOREIGN PATENT DOCUMENTS

| | | |
|---|---|---|
| EP | 0 780 134 A1 | 6/1997 |
| EP | 2 842 512 A1 | 3/2015 |
| WO | WO 96/28858 | 9/1996 |
| WO | WO 96/40341 | 12/1996 |

* cited by examiner

RACK MODULE AND RACK

The present application is a U.S. National Stage of PCT international Patent Application No. PCT/EP2016/073708, filed Oct. 5, 2016, which claims priority to EP Application No. 15306596, filed Oct. 9, 2015, both of which are hereby incorporated herein by reference.

The invention concerns a rack module for forming a support column, such as a rack, by stacking at least two rack modules, the rack module having at least one site for receiving a device for administering a medical product, this site comprising at least one plug for electric current supply to the administering device and for data transfer. It is also provided with an inlet connector and an outlet connector for connecting two successive modules to each other, power lines and data transfer lines connecting the inlet connector with the plug of the sites on the one hand side and with the outlet connector on the other hand side.

During medical treatments it may happen that several devices for administering medical products are connected to a same patient. These devices for administering medical products may be for example perfusion pumps or syringe-pumps. They are generally placed on above the other and fixed on a pole placed near the patient's bed. Each device must be connected to a power source. These devices are generally controlled by a computer what requires knowing the current status of the other devices. Therefore, the different devices are connected to a central unit. This leads to an important number of power lines and of data transfer lines which renders difficult the putting in place and the control of the whole.

In order to simplify the connection of the different administering devices, document WO 96/40341 proposes to connect electrically the lower device to the power source and to connect the other administering devices on the device which is directly placed under it. This reduces the number of power lines to one for the all the administering devices. Likewise, the cables connecting a device to the device directly under it allow data transfer between the devices. This arrangement allows also reducing the number of data transfer lines.

In order to facilitate even more the handling, racks have been conceived on which a plurality of administering devices can be fixed. A rack consists of a column provided with a plurality of supports and of connection plugs for receiving and connecting administering devices. Such a rack is for example known from document DE 40 30 368 C1. The rack is provided with an electric power cable in order to connect it to the electric power source, e.g. the electric circuit. It is also provided with a data transfer cable which can be coupled to a central unit. Each plug is connected inside the rack to a cable with an electric power line and a data transfer line. Each electric power line is connected to the general power supply of the rack, whereas each data transfer line is connected to the data transfer cable. Hence, it is possible to a centralized control and command of all administering devices fixed on the rack. This rack presents a large number of support units so that it has a certain height. However, it is not in all cases necessary to have such a big number of support units.

The document DE 199 40 526 C1 proposes therefore to divide the rack into a plurality of rack modules which can be superposed and connected to each other. The modules are all identical. Each module has three sites for administering devices. An inlet connector and an outlet connector are provided, the first one on the lower side of the module, the second one on the upper side of the module. Each site is provided with a plug for electric power supply and data transfer. Two sets of supplementary cables connect moreover the inlet connector and the outlet connector. The upper end of the first set of supplementary cables is connected to the outlet contact ports corresponding to the ports for the connection of the plugs of the three sites of a further module. The upper end of the second set of supplementary cables is connected to the outlet contact ports corresponding to the ports for the connection of the first set of supplementary cables of the further module. When a second module is placed on the first one so that its inlet connector is connected to the outlet connector of the first module, the first set of supplementary cables of the first module is connected to the cables of the three sites of the second module, whereas the second set of supplementary cables of the first module is connected to the first set of supplementary cables of the second module. Hence, it is possible to put a third module on the second one. The three sites of the third module shall be connected via the first set of supplementary cables of the second module to the second set of supplementary cables of the first module which itself is connected to the inlet connector of the first module. A data transmission and power supply cable connects the inlet connector of the first module to a central unit. According to the requirements, one, two or three superposed racks shall be used.

The object of the invention is to improve the connection between the rack modules in order to make its use easier. A further object of the invention is to make sure that at least one of the inlet and outlet connectors is protected when not in use.

These objects are achieved according to the invention in that the inlet connector or the outlet connector is movable between a stocking position and a connected position, the movable connector being called mobile connector and the other connector being called second connector, wherein, when a second module is placed over or under the module, the mobile connector in the connected position is in connection with the second connector of a second module placed over or under the module. This allows to stock in a safe position one of the connectors so that during the stocking and the handling of the module there is no risk for it to be damaged.

In order to facilitate the handling of the mobile connector, it is preferable to place it into a swivelling coupling. The mobile connector can be put away in a position in which it is protected and in which it does not hinder the stocking of the rack module.

According to an embodiment of the invention, means are provided for making the mobile connector pass from the stocking position to the connected position by swivelling in a plane perpendicular to the plugging-in direction of the mobile connector and of the second connector of the second module.

This can be realized in that the means for making the mobile connector pass from the stocking position to the connected position comprise a rod able to swivel around its longitudinal axis which is parallel to the plugging-in direction, the rod being movable in translation along this longitudinal axis at least over a length sufficient for the plugging-in of the mobile connector and of the second connector of the second module, the mobile connector being mounted on said rod.

Alternatively, the mobile connector can be mounted swivelling around an axis which is perpendicular to the plugging-in direction of the mobile connector and of the second connector of the second module.

The mobile connector and the second connector are preferably placed on a lateral face of the module with respect to the sites, but it is also possible that both the mobile connector and the second connector are placed on the same face of the module as the sites or on the face opposed to the one of the sites.

According to the present invention, the mobile connector and the second connector are preferably placed one near the top of the module and the other one near the bottom of the module.

Preferably, the mobile connector is the outlet connector and the second connector is the inlet connector. In this context, the mobile connector should be placed near the top of the module and the second connector near the bottom of the module.

Fitting means can be provided for facilitating the positioning of two successive rack modules, these fitting means consisting preferably of a groove and a rib, one being placed on the top of the housing and the other one on the bottom thereof. Means for fixing the module on a pole can also be provided on the rear side of the housing.

The invention also concerns a rack comprising at least two rack modules according to the invention, wherein the mobile connector of the first rack module is in the connected position, the mobile connector of the first rack module and the second connector of the second rack module being plugged together.

Figure 2:
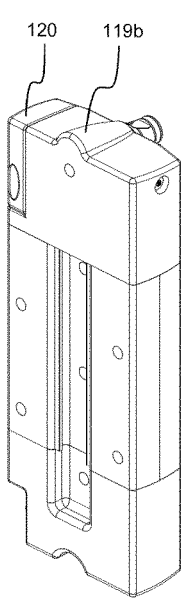
Figure 3:
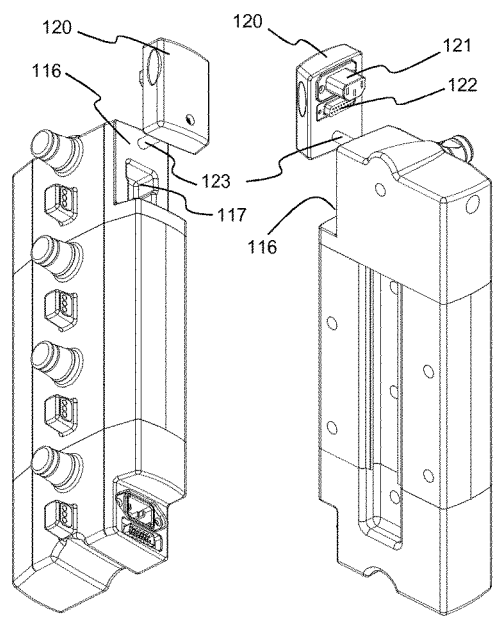
Figure 4:
Figure 5:
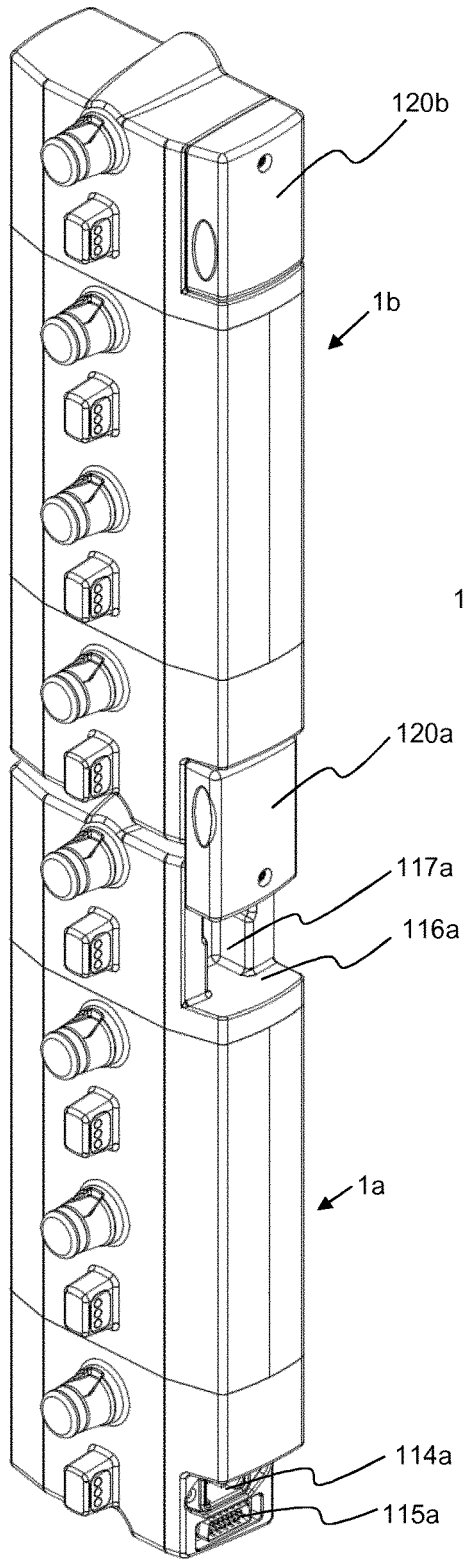
Figure 9:
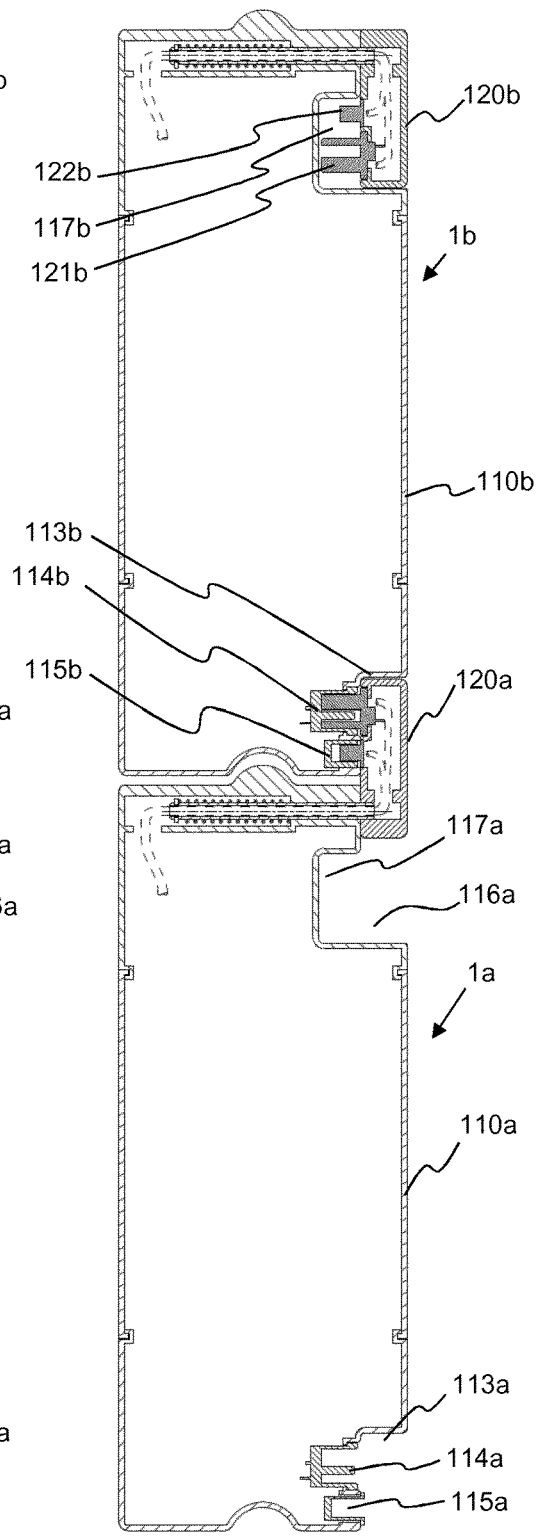
Figure 8:
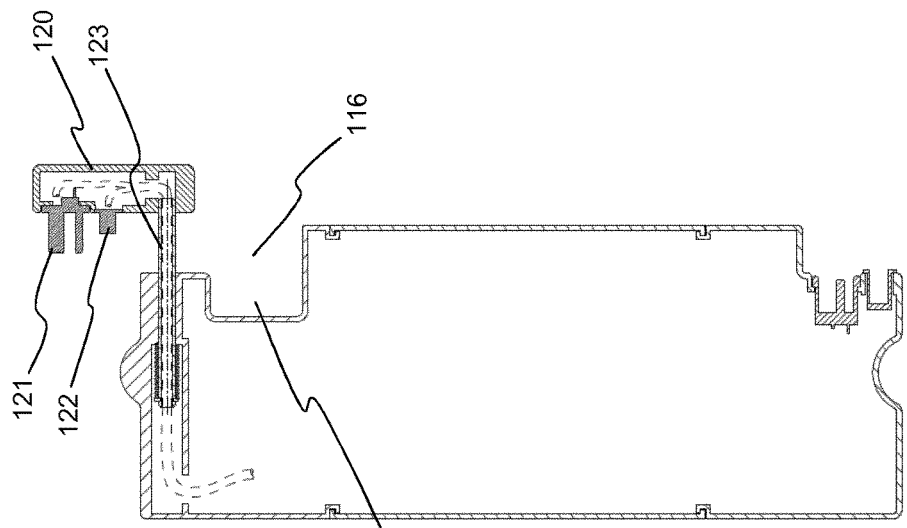
Figure 7:
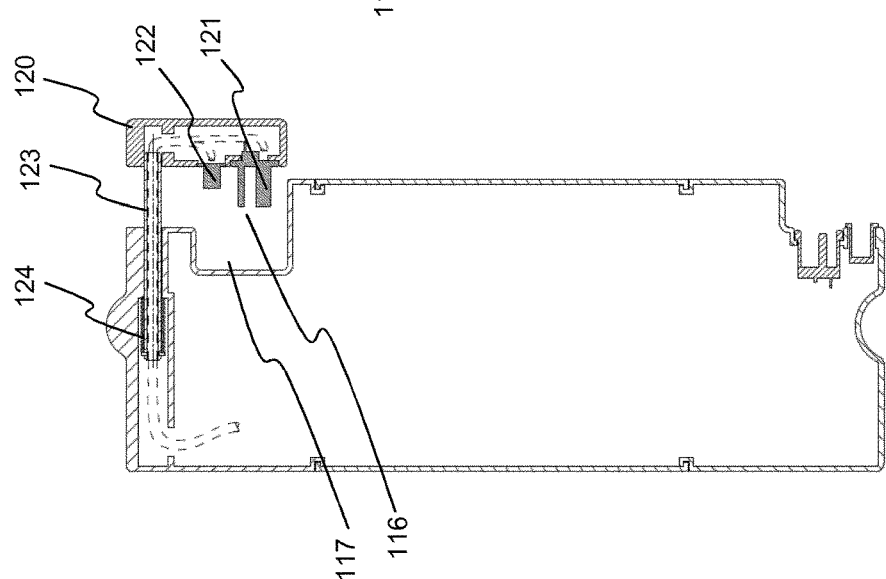
Figure 6:
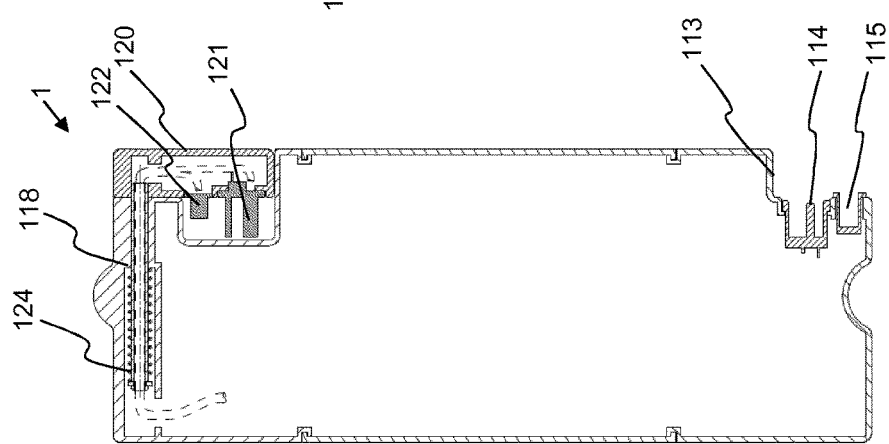
Figure 10:
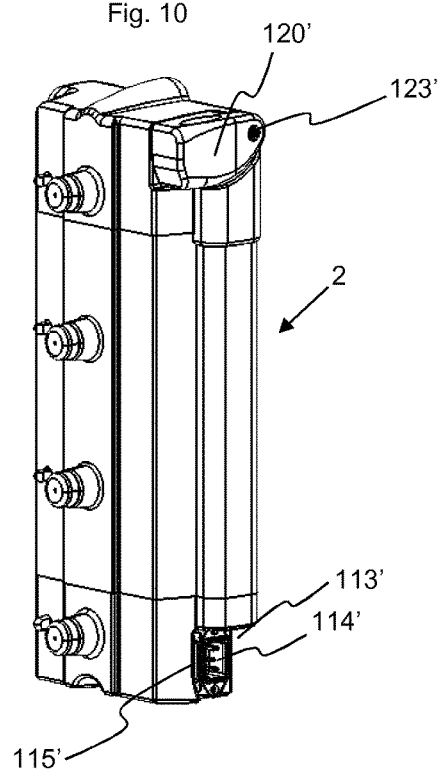
Figure 12:
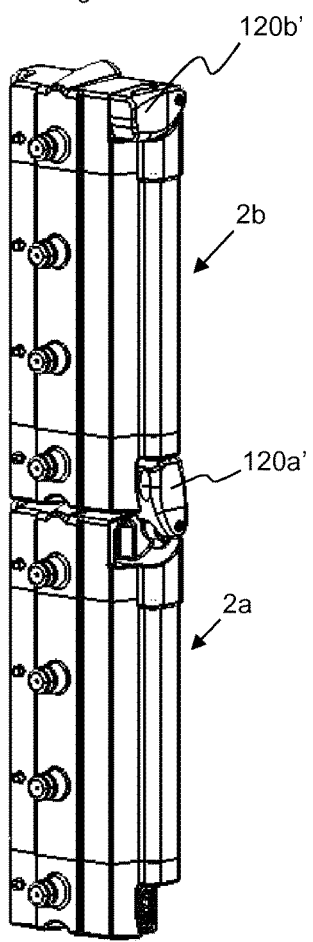
Figure 11:
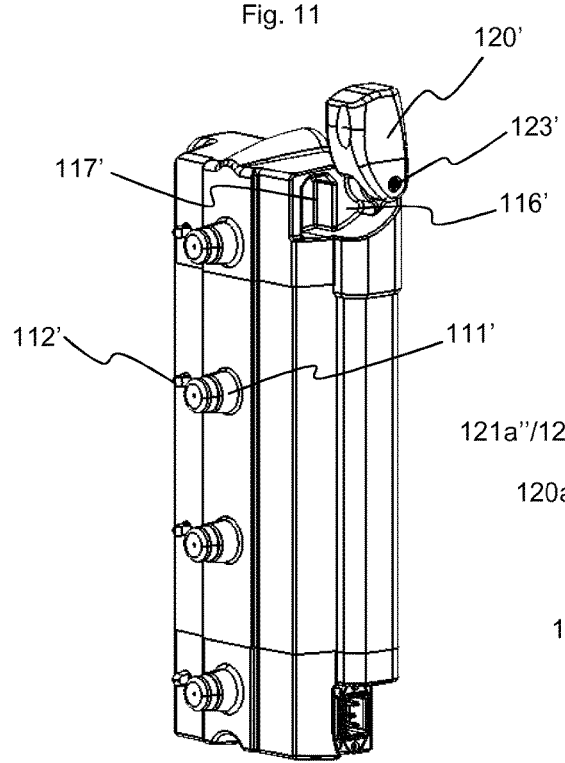
Figure 13:
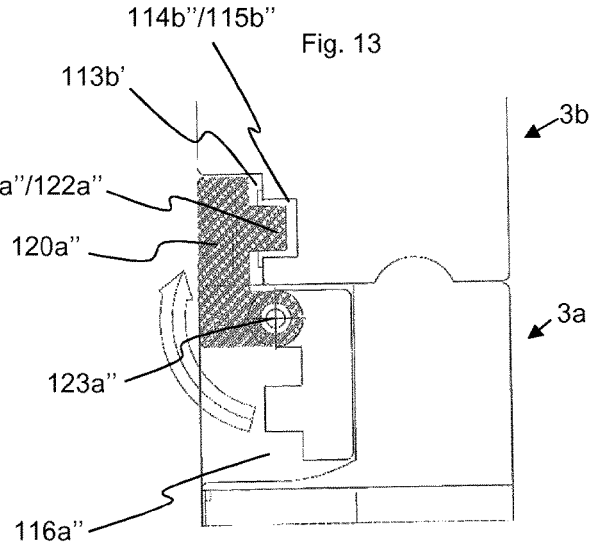

The invention is hereafter described more in detail with reference to an example of execution. The figures show:

FIG. 1: a perspective front view of a rack module, the mobile connector being in the stocking position;

FIG. 2: the module of FIG. 1 shown in rear perspective view, the mobile connector being in the stocking position;

FIG. 3: the same view as in FIG. 1, the mobile connector being in discarded and redressed position;

FIG. 4: the same view as in FIG. 2, the mobile connector being in discarded and redressed position;

FIG. 5: a perspective view of the two modules placed one on the other forming a rack, the mobile connector of the lower module being introduced into the second connector of the upper module;

FIG. 6: a sectional view of the module of FIG. 1, the mobile connector being in the stocking position;

FIG. 7: the same view as in FIG. 6, the mobile connector being in the lower discarded position;

FIG. 8: the same view as in FIG. 6, the mobile connector being in the upper discarded position;

FIG. 9: a sectional view of the two modules of FIG. 5, the mobile connector of the lower module being introduced into the second connector of the upper module;

FIG. 10: a perspective front view of a second example of execution of a module according to the invention, the mobile connector being in the stocking position;

FIG. 11: the same view as in FIG. 10, the mobile connector being in the upright position;

FIG. 12: a perspective view of the two modules of the second example of execution placed on the other, the mobile connector of the lower module being introduced into the second connector of the upper module;

FIG. 13: a schematic view of a third example of execution of the invention.

In a same embodiment, all modules are identical at least in regard to the inlet connectors and the outlet connectors. In order to distinguish the elements of a first module (1a, 2a, 3a) from those of a second module (1b, 2b, 3b), the letter "b" is added to the references of the second module.

The invention is described in detail with reference to the first embodiment (1a, 1b) represented in FIGS. 1 to 9. The other embodiments (2a, 2b, 3a, 3b) distinguish from this first embodiment in the design and the mode of pivoting of the mobile connector. The same elements have the same reference numbers, if applicable completed by the mention "'" for the second example of execution or by the mention "''" for the third one.

The module (1a, 1b) of the first embodiment comprises a housing (110) which is essentially of parallelepiped design and which has on its front face a plurality of sites for receiving the administering devices which are not represented. There is a support (111) corresponding to each site for receiving the administering device and a plug (112). The housing (110) has at is lower right angle a first recess (113) which extends over the whole width of the housing. This recess is limited by a vertical wall and by a horizontal wall. A female plug (114) for the electric power supply and a male plug (115) of the type D-sub connector for data transfer are placed in the vertical wall of the recess (113). These plugs form an inlet connector. The housing (110) moreover presents in the upper right angle a second recess (116) which extends over the whole width of the housing. Like the first one, this second recess is limited by a vertical wall and by a horizontal wall. The vertical walls of the two recesses are preferably aligned. A hole (117) is provided in the vertical wall of the second recess (116).

A coupling (120) is placed movably in the second recess. This coupling is provided on its face directed to the vertical face of the second recess (116) with a male plug (121) for electric power supply and with a female plug of D-sub type for data transfer. These plugs form an outlet connector. They also form the mobile connector in opposition to the second connector which is fixed and formed by the inlet connector (114, 115).

The coupling (120) is mounted on a rod (123) which penetrates horizontally into the housing (110) crossing the vertical wall of the second recess (116) sensibly in its vertical mid-plane. This rod can pivot freely around its longitudinal axis and can be moved in translation along this axis. A spring (124) is placed at its free extremity. It cooperates with an abutment (118) placed on the inside of the housing so that in absence of any constraint the rod (123) and together with it the coupling tend to move towards the inside of the housing, i.e. towards the left on the FIGS. 6 to 9.

The coupling (120) can pass from a stocking position represented in FIGS. 1, 2 and 6, to a connection position represented in FIGS. 5 and 9. In the stocking position, the electric power plug (121) and the D-sub connector (122) of the coupling (120) are placed in the hole (117) of the second recess (116). The coupling (120) is pushed against the vertical wall of the second recess under the effect of the spring (124). The external dimension of the coupling are chosen in such a way that in this stocking position the coupling fills out the second recess (116) and is located in the continuation of the four walls of the housing (front, rear, upper and lower wall).

Starting from the stocking position, it is possible to discard the coupling (120) from the vertical wall of the recess by pulling it towards the right side. This position is shown in FIG. 7. The electric power plug (121) and the D-sub connector (122) are then outside the hole (117). It is possible to make the coupling (120) pivot to the top around the rotation axis constituted by the rod (123). This position is shown in FIGS. 3, 4 and 8. If a second module (1b) is placed onto the first one (1a), the electric power plug (121) and the D-sub connector (122) constituting the outlet connector of the first module (1a) are aligned with the plug (114b) and the D-sub connector (115b) of the first recess (113b) of the second module (1b) which constitute the inlet connector of the second module (1b). It only remains to release the coupling (120) which under the effect of the spring (124) presses itself against the vertical wall of the second recess (113b) of the second module (1b) plugging together the two electric power plugs (114b, 121) on the one hand side and the two D-sub connectors (115b, 122) on the other hand side. This situation is shown in FIGS. 5 and 9.

It will be understood that the rotation axis constituted by the rod (123) is parallel to the direction of plugging-in of the electric power male plug (121) into the electric power female plug (114b) and of the D-sub male connector (115b) into the D-sub female connector (122). In consequence, the rotation of the coupling (120) bearing the mobile connector (121, 122) is done in a perpendicular plane to this plugging-in direction.

In a module the cables for the electric power supply and the data transfer are connected on the one hand side to the electric power plug (114) and to the D-sub connector (115) of the inlet connector placed in the lower recess (113) and on the other hand side to the electric power plug (121) and to the D-sub connector (122) of the outlet connector placed in the coupling (120) passing through the rod (123). The plugs (112) for the administering devices are also connected to the electric power plug (114) and to the D-sub connector (115) of the inlet connector.

Generally, means for fixing the module on a pole are provided on the rear side of the housing. These means are not shown in the figures. In order to facilitate the alignment of the successive modules, fitting means are provided which are constituted of a groove (119a) placed on the lower side of the housing and of a rib (119b) of complementary design placed on the upper side. In the example which is shown here, the groove and the rib are tapered so that the second module aligns automatically with the first one upon entry into contact thereof due to the curving of the truncated cone. Moreover, there will be no fitting if the second module is mounted upside down or if it is mounted hind-foremost.

It is possible to provide means for limiting the rotation movement of the coupling to about 180° by passing only on one side of the housing, e.g. by passing on the front in order to avoid that the cables leading to the coupling (120) get twisted by turning the coupling around itself.

The second embodiment (2a, 2b) shown in FIGS. 10 to 12 works in the same way. It has the same elements as the first one. It distinguishes from the first one only in the position of the rotation axis (123') of the coupling (120') and the design of the recesses (113', 116'). Here, the rotation axis is not centred like in the first embodiment, but it is placed further back. The pivoting amplitude of the coupling (120') is therefore lower than 180° and close to 90°. The hole (117') is sensibly perpendicular to the inlet connector (114', 115'). Like in the first case, the coupling (120') must first be discarded in order to get the outlet connector (121', 122') off the hole (117'), then set upright by pivoting it about 90° in order to align the outlet connector of the first module (2a) with the inlet connector of the second module (2b), then release the coupling (120') in order to make it press against the vertical wall of the recess plugging in the outlet coupling of the first module (2a) and the inlet coupling of the second module (2b). The back side of the horizontal wall of the second recess (116') is slightly curbed to the top so that the coupling (120') cannot make an entire turn around its rotation axis. This avoids twisting of the cables coupled to the coupling inside the module.

In the third embodiment (3a, 3b), the coupling (120") turns around an axis (123") perpendicular to the plugging-in direction of the connectors. The mobile coupling (120") is placed inside a recess (116") within which the axis is also located. After a turn of 180° to the top, the coupling (120") is placed in the recess (113b") of the second module (3b), the mobile connector (121", 122") of the first module (3a) and the second connector (114b", 115b") of the second module (3b) being plugged in each other.

It goes without saying that the mobile connector as well as the plugs and the corresponding recess could be placed on the left side of the housing instead of the right side or on the front side or the back side without modifying the invention. Likewise, the mobile coupling could be placed into the lower recess (113, 113', 113") instead of the upper recess (116, 116', 116") and instead of the outlet connector (121, 122, 121', 122', 121", 122"), the inlet connector (114, 115, 114', 115', 114", 115") could have been attributed to it.

Besides, the choice of the kind of plug and connector used is free in function of the needs and the evolution of the art. Moreover, the number of sites is not limited to four. It would be possible to foresee modules with 1, 2, 3, 5 or 6 sites for example. Furthermore, it is possible to have in a same embodiment rack modules with different numbers of sites, e.g. modules with two sites and modules with four sites. The rack modules are compatible with each other and can be combined freely since the inlet and the outlet connectors are identical.

The advantage of the present invention resides in the fact that the inlet connector being placed in a recess is protected and the outlet connector is also protected when it is placed in the hole. Hence, the module with its coupling in the protected position risks not to be damaged during the stocking and the handling thereof.

LIST OF REFERENCES

1 Module of the first embodiment
2 Module of the second embodiment
3 Module of the third embodiment
  110 Housing
    111 Support for administering device
    112 Plug for the administering device
    113 First recess
    114 Inlet plug for electric power supply
    115 Inlet plug for data transmission
    116 Second recess
    117 Hole
    118 Abutment for the spring
    119a Alignment groove
    119b Alignment rib
  120 Mobile coupling
    121 Outlet plug for electric power supply
    122 Outlet plug for data transfer
    123 Rod
    124 Spring

The invention claimed is:

1. A rack module for forming a support column by stacking at least two rack modules, the rack module comprising:
  at least one site for receiving a device for administering a medical product, the at least one site comprising at least one plug for electric power supply of the device for administering a medical product and for data transfer;
  one of the at least two rack modules having an inlet connector and an outlet connector for connecting the at least two rack modules to each other, power and data transfer lines connecting the inlet connector to the at least one plug of the at least one site on one side and the outlet connector on another side, one of the inlet connector and the outlet connector being movable between a stocking position and a connected position, the connector being movable being called a mobile connector and the other connector being called a second connector, wherein, when a second rack module is positioned over or under the rack module, the mobile connector in the connected position is in connection with the second connector of the second rack module positioned over or under the rack module, and the mobile connector in the stocking position is not in condition to connect with the second connector of a second rack module, and means for making the mobile connector pass from the stocking position to the connected position by swivelling in a plane perpendicular to a plugging-in direction of the mobile connector and of the second connector of the second rack module, the means for making the mobile connector pass from the stocking position to the connected position comprising a rod able to swivel around a longitudinal axis which is parallel to the plugging-in direction, the rod being movable in translation along the longitudinal axis at least over a length sufficient for plugging-in of the mobile connector and of the second connector of the second rack module, the mobile connector being mounted on said rod.

2. The rack module according to claim 1, wherein the mobile connector is placed into a swivelling coupling.

3. The rack module according to claim 1, wherein the mobile connector and the second connector are disposed on a lateral face of the rack module with respect to the at least one site.

4. The rack module according to claim 1, wherein both the mobile connector and the second connector are disposed on a same face of the rack module as the at least one site or on a face opposed to the one of the at least one site.

5. The rack module according to claim 1, wherein the mobile connector and the second connector are disposed one near an upper end of the rack module and another near a lower end of the rack module opposite the upper end.

6. The rack module according to claim 1, wherein the mobile connector is the outlet connector and the second connector is the inlet connector.

7. The rack module according to claim 6, wherein the mobile connector is disposed near an upper end of the rack module and the second connector near a lower end of the rack module opposite the upper end.

8. The rack module according to claim 1, further comprising fitting means for facilitating positioning of two successive rack modules, the fitting means comprising a groove and a rib, one of the groove and the rib being disposed on a top of a housing and another of the groove and the rib on a bottom thereof.

9. A rack comprising at least two rack modules according to claim 1, wherein the mobile connector of a first rack module is in the connected position, the mobile connector of the first rack module and the second connector of the second rack module being plugged together.

* * * * *